United States Patent
Mahesh et al.

(10) Patent No.: US 8,005,278 B2
(45) Date of Patent: Aug. 23, 2011

(54) SYSTEM AND METHOD FOR PATIENT ACUITY DRIVEN WORKFLOW USING COMPUTER-AIDED DIAGNOSIS OF MEDICAL IMAGES

(75) Inventors: Prakash Mahesh, Hoffman Estates, IL (US); Murali Kumaran Kariathungal, Hoffman Estates, IL (US); Mark M. Morita, Arlington Heights, IL (US)

(73) Assignee: General Electric Company, Schenectady, NY (US)

(*) Notice: Subject to any disclaimer, the term of this patent is extended or adjusted under 35 U.S.C. 154(b) by 868 days.

(21) Appl. No.: 11/286,946

(22) Filed: Nov. 22, 2005

(65) Prior Publication Data

US 2007/0116336 A1    May 24, 2007

(51) Int. Cl.
*G06K 9/00* (2006.01)
(52) U.S. Cl. ...................................... 382/128
(58) Field of Classification Search .......... 382/128–132, 382/190; 600/407–408; 128/920, 922, 925; 706/20, 16
See application file for complete search history.

(56) References Cited

U.S. PATENT DOCUMENTS

| | | | | |
|---|---|---|---|---|
| 5,873,824 | A * | 2/1999 | Doi et al. | 600/408 |
| 6,058,322 | A * | 5/2000 | Nishikawa et al. | 600/408 |
| 7,162,061 | B1 * | 1/2007 | Takeo | 382/128 |
| 7,295,691 | B2 * | 11/2007 | Uppaluri et al. | 382/130 |
| 7,298,881 | B2 * | 11/2007 | Giger et al. | 382/128 |
| 2003/0103663 | A1 * | 6/2003 | Li et al. | 382/131 |
| 2005/0234570 | A1 * | 10/2005 | Horsch et al. | 700/93 |
| 2006/0210133 | A1 * | 9/2006 | Krishnan et al. | 382/128 |
| 2007/0041623 | A1 * | 2/2007 | Roehrig et al. | 382/128 |
| 2007/0083849 | A1 * | 4/2007 | Stoval, III | 717/104 |

OTHER PUBLICATIONS

Web page for R2 Home, http://www.r2tech.com/.
Web page for R2 What is CAD?, http://www.r2tech.com/main/info/what_is_cad.php.

* cited by examiner

*Primary Examiner* — Vu Le
*Assistant Examiner* — Andrae S Allison
(74) *Attorney, Agent, or Firm* — McAndrews, Held & Malloy, Ltd.; Michael A. Dellapenna

(57) ABSTRACT

Systems for determining patient acuity including an analysis component, an acuity database, and a processing component are provided. The analysis component is capable of generating analysis data based at least in part on a medical image. The acuity database is capable of associating the analysis data with an acuity value. The processing component is capable of generating an acuity level based at least in part on the acuity value.

19 Claims, 4 Drawing Sheets

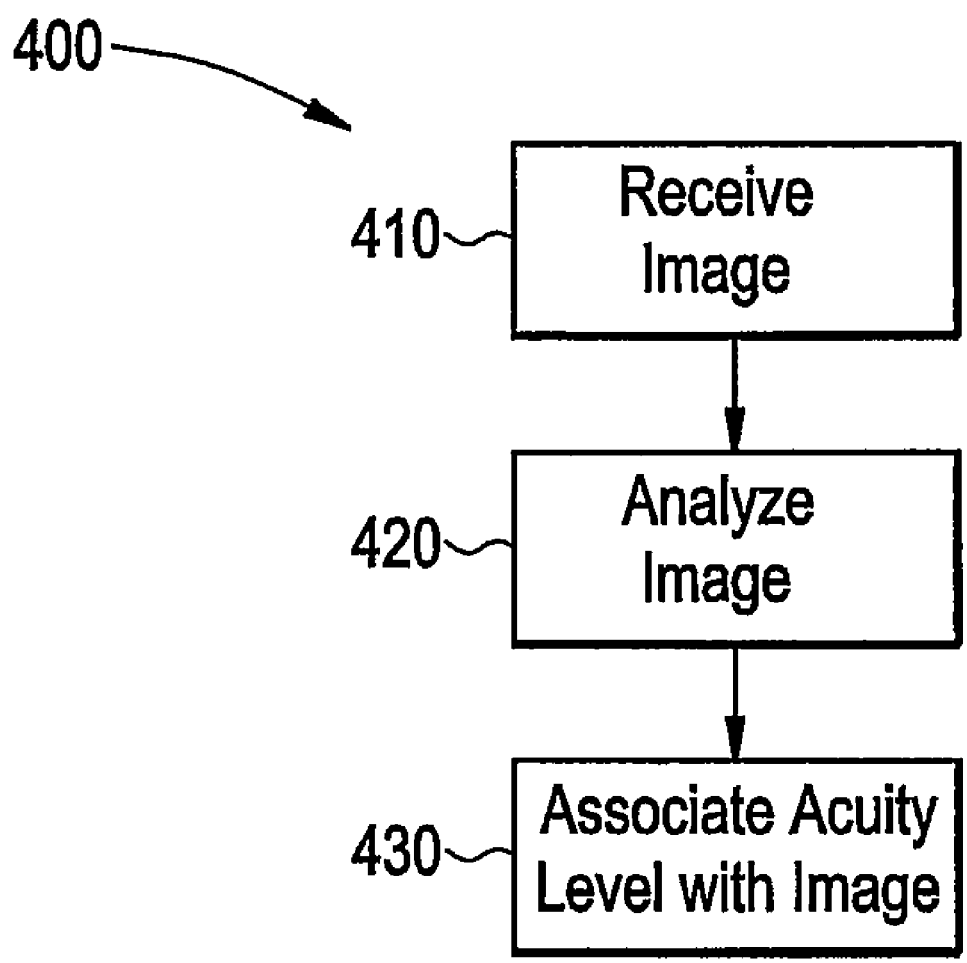

SYSTEM AND METHOD FOR PATIENT ACUITY DRIVEN WORKFLOW USING COMPUTER-AIDED DIAGNOSIS OF MEDICAL IMAGES

BACKGROUND OF THE INVENTION

The present invention generally relates to medical workflow. In particular, the present invention relates to a system and method for patient acuity driven workflow using computer-aided diagnosis of medial images.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

PACS connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining health-care operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools.

Computer-aided diagnosis (CAD) of image data may be utilized by practitioners to aid in reading medical images. CAD software can identify and mark features, abnormalities, and/or anomalies in medical images to bring to the attention of the practitioner. In addition, CAD software can generate a report of the identified features, abnormalities, and/or anomalies. The practitioner may then review the marked images and/or reports prior to making a final diagnosis.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in inefficient workflow and service to clients, which may impact a patient's health and safety or result in liability for a healthcare facility. Data entry and access is also complicated in a typical healthcare facility.

With increasing volumes of examinations and images, a reduction of radiologists, and mounting pressures on improving productivity, radiologists and other healthcare personnel are in need of image processing or display workflow enhancements that aid in prioritizing workflow. Currently, healthcare personnel utilize worklists to organize and priorities their workflow. Worklists show a list of exams or procedures. A worklist may list provide a list of exams for a radiologist to read, for example. Worklists may show new exams or procedures as new cases are created in the system. The worklist may allow the radiologist to organize the exams to be read based on time received or patient name, for example.

There is a need for workflow enhancements that allow a healthcare provider to attend to more acute cases first. Current systems only allow images for acute cases to be marked 'stat.' However, within the group of images marked as 'stat,' there is no indication or organization of which cases are more acute than others.

Therefore, there is a need for a system and method for patient acuity driven workflow using computer-aided diagnosis of medial images.

BRIEF SUMMARY OF THE INVENTION

Certain embodiments of the present invention provide a system for determining patient acuity including an analysis component, an acuity database, and a processing component. The analysis component is capable of generating analysis data based at least in part on a medical image. The acuity database is capable of associating the analysis data with an acuity value. The processing component is capable of generating an acuity level based at least in part on the acuity value.

Certain embodiments include a worklist in communication with the processing component. The worklist is capable of organizing worklist entries based at least in part on the acuity level. Certain embodiments include an imaging system database. The imaging system database is in communication with the processing component. The imaging system database is capable of storing the medical image associated with the acuity level. In an embodiment, the imaging system database includes an image database and an image acuity database. The medical image is stored in the image database. The acuity level is stored in the image acuity database. The image database is capable of associating a stored medical image with a stored acuity level. Certain embodiments include a worklist in communication with the imaging system database. The worklist is capable of organizing worklist entries based at least in part on the acuity level. In an embodiment, the worklist is capable of retrieving a stored medical image and the stored acuity level associated with the stored medical image from the imaging system database. Certain embodiments include an imaging system. The imaging system generates the medical image. In an embodiment, the analysis component includes a computer-aided diagnosis (CAD) component. In an embodiment, the acuity database is capable of being customized for a specific healthcare facility.

Certain embodiments of the present invention provide a method for determining patient acuity including receiving a medical image, analyzing the medical image to generate analysis data, and associating an acuity level with the medical image based at least in part on the analysis data and an acuity database.

Certain embodiments include receiving the medical image from an imaging system. Certain embodiments include organizing a worklist based at least in part on the acuity level. Certain embodiments include storing the medical image and the associated acuity level in an imaging system database. In an embodiment, the analyzing step is performed with an analysis component. In an embodiment, the analysis component includes a computer-aided diagnosis (CAD) component. Certain embodiments include including mapping the analysis data to an acuity value based at least in part on the acuity database. The acuity level is based at least in part on the acuity value.

Certain embodiments of the present invention provide a computer-readable medium including a set of instructions for execution on a computer, the set of instructions including an analysis routine configured to analyze a medical image and generating analysis data and a processing routine configured to generate an acuity level based at least in part on the analysis data.

In an embodiment, the processing routine is configured to use an acuity database to generate the acuity level. In an embodiment, the processing routine is configured to associate the acuity level with the medical image. Certain embodiments include a worklist routine. The worklist routine is configured to organize worklist entries based at least in part on the acuity level.

BRIEF DESCRIPTION OF SEVERAL VIEWS OF THE DRAWINGS

FIG. 4 illustrates a flow diagram for a method for determining patient acuity in accordance with an embodiment of the present invention.

Figure 1:
FIG. 1 illustrates a current worklist interface.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a current worklist interface 100. The worklist interface 100 includes rows for each entry 110 in the worklist. The worklist interface 100 includes columns 120 that separate fields in each worklist entry 110.

In operation, a user may use the worklist interface 100 to view, organize, and/or process entries 110 in the user's worklist. A user may be a physician, radiologist, technician, or other healthcare provider, for example. A worklist entry 110 may correspond to a particular patient, procedure, study, and/or set of images, for example. For example, a radiologist may utilize worklist interface 100 to view the sets of images, as indicated by each entry 110 in the worklist, he has to read. Selecting a worklist entry 110 may bring up one or more images associated with the entry. For example, a radiologist may select a worklist entry 110 to read a set of CT image slices associated with that entry.

The columns 120 in the worklist interface 100 correspond to fields in each worklist entry 110. Columns 120 may correspond to fields such as, for example, patient name, patient identifier, procedure, and modality.

The worklist interface 110 may provide various mechanisms to organize worklist entries 110. For example, a user may select a button in the interface 110 to display recent exams. As another example, a user may select a button in the interface 110 to display unread exams. As another example, a worklist may be sorted using the worklist columns 120. For example, a radiologist may utilize worklist interface 100 to sort worklist entries 110 by patient name by selecting the "patient name" column 120 to locate an entry 110 for a particular patient to see the corresponding procedure information.

Figure 2:
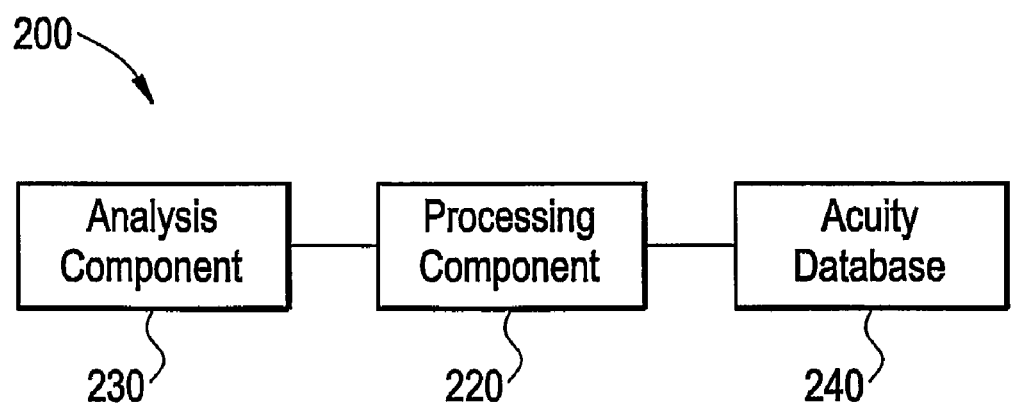
FIG. 2 illustrates a system for determining patient acuity used in accordance with an embodiment of the present invention.

FIG. 2 illustrates a system 200 for determining patient acuity used in accordance with an embodiment of the present invention. The system 200 includes a processing component 220, an analysis component 230, and an acuity database 240. The processing component 220 is in communication with the analysis component 230. The processing component 220 is in communication with the acuity database 240.

In operation, the analysis component 230 receives a medical image. The medical image may be received from the processing component 220. The medical image may be provided by an acquisition modality (not shown) such as an imaging system. An imaging system may include, for example, a CT scanner and/or an MR scanner. As another example, the acquisition modality may generate the medical image from a three-dimensional volumetric data set. As another example, the medical image may be received from a PACS or RIS.

The analysis component 230 may receive a set of medical images. That is, in an embodiment, the analysis component 230 may receive one or more medical images. For example, rather than receiving a single CT slice, the analysis component 230 may receive a set of generated image slices. The following discusses the case of a single medical image, but it would be understood by one having ordinary skill in the art that a set of images may also be similarly processed.

The analysis component 230 generates analysis data based at least in part on the medical image. The analysis component 230 may analyze the medical image for anomalies and/or abnormalities and then generate analysis data describing those anomalies. For example, the analysis component 230 may analyze a medical image and determine that the image shows a 5 mm cancerous lump in the left lung. The analysis component 230 may then generate analysis data that includes, for example, the size, body part, position, orientation, and/or malignancy information regarding the anomaly and/or abnormality. The analysis data may include information regarding more than one anomaly. In an embodiment, the analysis component 230 includes and/or is part of a computer-aided diagnosis (CAD) system.

The processing component 220 receives the analysis data from the analysis component 230. The processing component 220 generates an acuity level. The acuity level may be associated with a medical image. For example, the acuity level may be associated with the medical image analyzed by the analysis component 230, described above. The acuity level may correspond, at least in part, to the severity of an abnormality and/or anomaly in the medical image, for example.

In an embodiment, the processing component 220 generates the acuity level based at least in part on the acuity database 240. The processing component 220 may look up an acuity value in the acuity database 240 based at least in part on analysis data received from the analysis component 230. For example, the processing component 220 may receive analysis data from the analysis component 230 that indicates the possible presence of a 8 mm malignant tumor in the patient's lung. Based at least in part on the location, orientation, body position, size, and/or type of the anomaly and/or abnormality, the processing component may look up an appropriate entry in the acuity database 240 to determine an associated acuity value. For example, an 8 mm tumor in the lung may correspond to an acuity value of 4 in the acuity database 240. The acuity level generated by the processing component 220 may be based at least in part on the acuity value. For example, the generated acuity level may be the same as the acuity value. As another example, the generated acuity level may be a scaled representation of the acuity value.

In an embodiment, the acuity database 240 is a knowledge base. In an embodiment, the acuity database 240 is a table or other data structure. In an embodiment, the acuity database 240 is customized for a specific healthcare facility. For example, an oncology clinic may assign different or more fine-grained acuity values to a broader or more detailed list of anomalies and/or abnormalities than a general care facility.

In certain embodiments, the processing component 220 looks up or retrieves an acuity value in the acuity database 240 based at least in part on analysis data. In certain embodiments, the acuity database 240 provides the processing component 220 with an acuity value based at least in part on analysis data. The analysis data may be mapped to a corresponding acuity value, for example.

The analysis data may indicate more than one anomaly and/or abnormality. In an embodiment, the processing component 220 may generate an acuity level corresponding to the highest acuity value assigned to the appropriate entries in the acuity database 240. In an embodiment, the processing component 220 may generate an acuity level based at least in part on a computation. The computation may include, for example, the sum, product, average, and/or weighted combination, of one or more of the acuity values. For example, if two tumors are indicated in the analysis data, one with a corresponding acuity value of 2 and the other with a corresponding acuity value of 3, the processing component 220 may generate an acuity level of 5 (the sum of the two corresponding acuity values).

In an embodiment, the processing component 220 provides a medical image to the analysis component 230 to analyze. The medical image may be received from an acquisition modality such as an imaging system. An imaging system may include, for example, a CT scanner and/or an MR scanner. As another example, the acquisition modality may generate the medical image from a three-dimensional volumetric data set. As another example, the medical image may be received from a PACS or RIS.

The components, elements, and/or functionality of system 200 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

Figure 3:
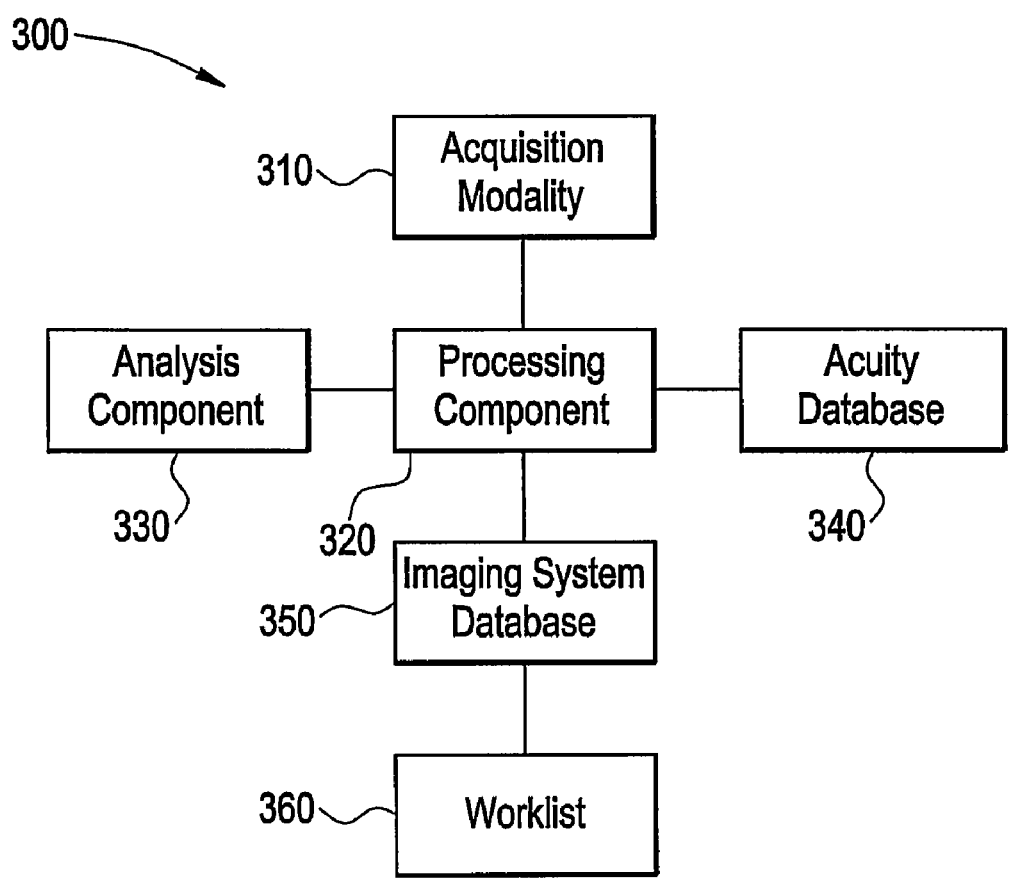
FIG. 3 illustrates a system for determining patient acuity used in accordance with an embodiment of the present invention.

FIG. 3 illustrates a system 300 for determining patient acuity used in accordance with an embodiment of the present invention. The system 300 includes an acquisition modality 310, a processing component 320, an analysis component 330, an acuity database 340, an imaging system database 350, and a worklist 360.

The acquisition modality 310 is in communication with the processing component 320. The processing component 320 is in communication with the analysis component 330. The processing component 320 is in communication with the acuity database 340. The imaging system database 350 is in communication with the processing component 320. The worklist 360 is in communication with the imaging system database 350.

The processing component 320 may be similar to the processing component 220, described above, for example. The analysis component 330 may be similar to the analysis component 230, described above, for example. The acuity database 340 may be similar to the acuity database 240, described above, for example.

In operation, the acquisition modality 310 supplies a medical image to the processing component 320. The acquisition modality may be, for example, an imaging system such as, for example, a CT scanner and/or an MR scanner. As another example, the acquisition modality may generate the medical image from a three-dimensional volumetric data set. The acquisition modality 310 may be similar to the acquisition modality discussed above, for example.

The acquisition modality 310 may generate a set of medical images. That is, in an embodiment, the acquisition modality 310 may provide one or more medical images. For example, rather than generating a single CT slice, the acquisition modality 310 may provide a set of generated image slices. The following discusses the case of a single medical image, but it would be understood by one having ordinary skill in the art that a set of images may also be similarly processed.

The processing component 320 receives the medical image from the acquisition modality 310. The processing component 320 may communicate the medical image to the analysis component 330. Alternatively, the analysis component 330 receives the medical image from the acquisition modality 310. In either case, the operation of processing component 320, analysis component 330, and acuity database 340 is similar to the operation of processing component 220, analysis component 230, and acuity database 240, respectively, described above.

In an embodiment, the processing component 320 communicates the generated acuity level to the imaging system database 350. In an embodiment, the processing component 320 communicates the medical image to the imaging system database 350. In an embodiment, the processing component 320 associates the acuity level with the medical image. In an embodiment, the processing component 320 communicates the acuity level associated with the medical image to the imaging system database 350.

The imaging system database 350 may associate the acuity level with the medical image. For example, the imaging system database 350 may store the medical image and the associated acuity level. In an embodiment, the imaging system database 350 stores the medical image and the associated acuity level in the same database table. In an embodiment, the imaging system database 350 stores the medical image in a first database table along with a reference to the associated acuity level, where the associated acuity level is stored in a second database table. The imaging system database 350 may be part of a PACS or RIS, for example.

In certain embodiments, the imaging system database 350 includes and/or utilizes an image database and an image acuity database. The imaging system database 350 may store the medical image received from the processing component 320 in the image database, for example. The imaging system database 350 may store the acuity level received from the processing component 320 in the image acuity database, for example. In an embodiment, the image database contains a reference to the associated acuity level stored in the image acuity database. In an embodiment, the image acuity database contains a reference to the associated image stored in the image database.

Worklist 360 is capable of displaying worklist entries. For example, the worklist entries may correspond to particular patients or exams for a radiologist to read. Worklist 360 may include an interface similar to worklist interface 100, described above, for example.

Worklist 360 may retrieve a medical image from the imaging system database 350. Worklist 360 may retrieve the medical image in response to a user's request, for example. As another example, worklist 360 may retrieve the medical image automatically, to progress through worklist entries. Worklist 360 may display the retrieved medical image to a user, for example.

In certain embodiments, worklist 360 may retrieve acuity information from the imaging system database 350. In certain embodiments, worklist 360 may retrieve a medical image and the acuity level associated with the medical image from the imaging system database 350.

In certain embodiments, worklist 360 is in communication with processing component 320. In an embodiment, imaging system database 350 is not present. Worklist 360 may receive the medical image and/or the acuity level from processing component 320.

In certain embodiments, worklist 360 provides a representation of the acuity level associated with an image referenced by a worklist entry. For example, worklist 360 may display a column for acuity level. As another example, worklist 360 may color-code worklist entries based at least in part on acuity level. In an embodiment, worklist 360 allows worklist entries to be sorted based on acuity level. For example, worklist 360 may display worklist entries from highest to lowest acuity level. In an embodiment, worklist 360 is automatically sorted based on the acuity level.

The components, elements, and/or functionality of system 300 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

FIG. 4 illustrates a flow diagram for a method 400 for determining patient acuity in accordance with an embodiment of the present invention. The method 400 includes the following steps, which will be described below in more detail. First, at step 410, an image is received. Then, at step 420, the image is analyzed. Next, at step 430, an acuity level is associated with the image. The method 400 is described with reference to elements of systems described above, but it should be understood that other implementations are possible.

First, at step 410, an image is received. The image may be received from a processing component. The processing component may be similar to processing component 220, described above, for example. The processing component may be similar to processing component 320, described above, for example. The image may be received from an acquisition modality such as an imaging system. An imaging system may include, for example, a CT scanner and/or an MR scanner. As another example, the acquisition modality may generate the image from a three-dimensional volumetric data set. As another example, the image may be received from a PACS or RIS.

In an embodiment, the image is received at a processing component. The processing component may be similar to processing components 220 and/or 320, described above, for example. In an embodiment, the image is received at an analysis component. The analysis component may be similar to analysis component 230, described above, for example. The analysis component may be similar to analysis component 330, described above, for example Then, at step 420, the image is analyzed. The image may be analyzed by an analysis component. The analysis component may be similar to analysis components 230 and/or 330, described above, for example. The image is analyzed to produce analysis data.

The image may be analyzed for anomalies and/or abnormalities, for example. Analysis data may then be generated describing those anomalies. For example, the image may be analyzed by an analysis component and the analysis component may determine that the image shows a 5 mm cancerous lump in the left lung. The analysis component may then generate analysis data that includes, for example, the size, body part, position, orientation, and/or malignancy information regarding the anomaly and/or abnormality. The analysis data may include information regarding more than one anomaly. In an embodiment, the image is analyzed by a CAD system.

Next, at step 430, an acuity level is associated with the image. The acuity level may be generated by a processing component. The processing component may be similar to processing components 220 and/or 320, described above, for example. The acuity level may be associated with the image analyzed at step 420, for example. The acuity level may correspond, at least in part, to the severity of an abnormality and/or anomaly in the image, for example.

In an embodiment, the acuity level is based at least in part on an acuity database. The acuity database may be similar to the acuity databases 240 and/or 340, described above, for example.

In an embodiment, the acuity level is associated with the image by a processing component. The processing component may be similar to the processing components 220 and/or 320, described above, for example. In an embodiment, the acuity level is associated with the image by an imaging system database. The imaging system database may be similar to the imaging system database 350, described above, for example.

One or more of the steps of the method 400 may be implemented alone or in combination in hardware, firmware, and/or as a set of instructions in software, for example. Certain embodiments may be provided as a set of instructions residing on a computer-readable medium, such as a memory or hard disk, for execution on a computer or other processing device, such as, for example, a PACS workstation.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for determining patient acuity, the system including:
    an analysis component for generating analysis data based at least in part on a medical image;
    an acuity database for associating the analysis data with a plurality of acuity values, each acuity value based on a separate anomaly, thereby providing an acuity value for each separate anomaly; and
    a processing component for identifying a highest acuity value of the plurality of acuity values and associating an acuity level that corresponds to the highest acuity value with the medical image by mapping the analysis data to an acuity value based at least in part on the acuity database, wherein the acuity level is based at least in part on the acuity value.

2. The system of claim 1, further including a worklist, wherein the worklist is in communication with the processing component, wherein the worklist organizes worklist entries based at least in part on the acuity level.

3. The system of claim 1, further including an imaging system database, wherein the imaging system database is in communication with the processing component, wherein the imaging system database stores the medical image associated with the acuity level.

4. The system of claim 3, wherein the imaging system database includes an image database and an image acuity database, wherein the medical image is stored in the image database, wherein the acuity level is stored in the image acuity database, and wherein the image database associates with a stored medical image with a stored acuity level.

5. The system of claim 3, further including a worklist, wherein the worklist is in communication with the imaging system database, wherein the worklist organizes worklist entries based at least in part on the acuity level.

6. The system of 5, wherein the worklist is capable of retrieving a stored medical image and the stored acuity level associated with the stored medical image from the imaging system database.

7. The system of claim 1, further including an imaging system, wherein the imaging system generates the medical image.

8. The system of claim 1, wherein the analysis component includes a computer-aided diagnosis (CAD) component.

9. The system of claim 1, wherein the acuity database is customized for a specific healthcare facility.

10. A method for determining patient acuity, the method including:
    receiving a medical image;
    analyzing using a processor the medical image to generate analysis data;
    associating the analysis data with a plurality of acuity values using an acuity database, each acuity value based on a separate anomaly, thereby providing an acuity value for each separate anomaly;
    identifying a highest acuity value of the plurality of acuity values; and
    associating an acuity level that corresponds to the highest acuity value with the medical image by mapping the analysis data to an acuity value based at least in part on the acuity database, wherein the acuity level is based at least in part on the acuity value.

11. The method of claim 10, further including receiving the medical image from an acquisition modality.

12. The method of claim 10, further including organizing a worklist based at least in part on the acuity level.

13. The method of claim 10, further including storing the medical image and the associated acuity level in an imaging system database.

14. The method of claim 10, wherein the analyzing step is performed with an analysis component.

15. The method of claim 14, wherein the analysis component includes a computer-aided diagnosis (CAD) component.

16. A non-transitory computer-readable medium including a set of computer instructions for execution on a computer, the set of instructions including:
    an analysis routine configured to analyze a medical image, generate analysis data and associate the analysis data with a plurality of acuity values, each acuity value based on a separate anomaly, thereby providing an acuity value for each separate anomaly; and
    a processing routine configured to identify a highest acuity value of the plurality of acuity values and associate an acuity level that corresponds to the highest acuity value with the medical image by mapping the analysis data to an acuity value based at least in part on the acuity database, wherein the acuity level is based at least in part on the acuity value.

17. The set of instructions of claim 16, wherein the processing routine is configured to use an acuity database to generate the acuity level.

18. The set of instructions of claim 16, wherein the processing routine is configured to associate the acuity level with the medical image.

19. The set of instructions of claim 16, further including a worklist routine, wherein the worklist routine is configured to organize worklist entries based at least in part on the acuity level.

* * * * *